United States Patent [19]

Shibuya et al.

[11] Patent Number: 5,034,353
[45] Date of Patent: Jul. 23, 1991

[54] BIOCOMPATIBLE GLASS CERAMICS

[75] Inventors: Takehiro Shibuya, Shiga; Akira Matsui; Yoshinori Morita, both of Kyoto; Kiyoyuki Okunaga, Shiga; Masayuki Ninomiya, Osaka, all of Japan

[73] Assignee: Nippon Electric Glass Co. Ltd., Otsu, Japan

[21] Appl. No.: 443,743

[22] Filed: Nov. 30, 1989

[30] Foreign Application Priority Data

Dec. 1, 1988 [JP] Japan .................................. 63-306261

[51] Int. Cl.$^5$ ............................................. C03C 10/16
[52] U.S. Cl. ........................................ 501/3; 501/10; 106/35
[58] Field of Search ..................... 501/3, 10; 106/35

[56] References Cited

U.S. PATENT DOCUMENTS 3,922,155  11/1975  Broemer et al. ..................... 501/10
3,981,736   9/1976  Broemer et al. ..................... 501/10
4,786,617  11/1988  Andrieu et al. ...................... 501/3

Primary Examiner—Mark L. Bell
Assistant Examiner—Deborah Jones
Attorney, Agent, or Firm—Hopgood, Calimafde, Kalil, Blaustein & Judlowe

[57] ABSTRACT

A high-mechanical strength biocompatible crystallized glass essentially comprises both crystallines consisting of tetrasilicic fluorine mica series and calcium phosphate series. The crystallized glass has substantially non-sodium oxide and useful in a dental medical care, as repairing material of tooth.

3 Claims, No Drawings

BIOCOMPATIBLE GLASS CERAMICS

BACKGROUND OF THE INVENTION

The present invention relates to crystallized glass or glass ceramics and, in particular, to biocompatible glass which is useful for repair of destroyed portion of a tooth or aesthetic improvement of a tooth and others in a dental medical care.

It is needless to say that the biocompatible materials which are useful, for example, for tooth repairing materials, are required not to be harmful to living tissues such as human bodies and animal in bodies. Among the other various important requirements for such biocompatible materials are high mechanical strength and an excellent biological affinity.

Although mica series crystalline and calcium phosphate series like apatite are well known as typical and conventional biocompatible materials in the prior art (Japanese Patent Applications laid open under Nos. 199742/1984 and 10939/1987), they have disadvantages.

The mica series crystallized glass can not satisfy the requirements for excellent biological affinity and moreover has low dimensional accuracy.

The calcium phosphate series crystallized glass is insufficient insofar as mechanical strength is concerned, in particular, exhibits substantial degradation of strength due to a flaw or microcrack.

SUMMARY OF THE INVENTION

It is an object of the present invention to provide a crystallized glass, as a biocompatible material for use, for example, as a tooth repairing material, which has an markedly improved mechanical strength and markedly improved excellent biological affinity.

According to the present invention, a biocompatible crystallized glass is obtained which essentially comprises both crystallines consisting of tetrasilicic fluorine mica series and calcium phosphate series, the crystallized glass being substantially free of sodium oxide.

Preferably, the biocompatible crystallized glass composition consists essentially by weight of:
40.0–70.0% $SiO_2$,
5.0–34.0% $MgO$,
1.8–11.0% $F$,
0–2.0% $Al_2O_3$,
4.0–20.0% $K_2O$,
0–7.0% $ZrO_2$,
0.01–20.0% $CaO$, and
0.01–20.0% $P_2O_5$.

Alternatively, the biocompatible crystallized glass composition consists essentially by weight of:
42.0–65.0% $SiO_2$,
7.0–25.0% $MgO$,
2.5–8.0% $F$,
0–1.9% $Al_2O_3$,
8.0–18.0% $K_2O$,
0–6.0% $ZrO_2$,
0.5–10.0% $CaO$, and
0.5–10.0% $P_2O_5$.

DESCRIPTION OF THE PREFERRED EMBODIMENTS

In the biocompatible crystallized glass according to the present invention, both crystallines are essentially contained as tetrasilicic fluorine mica series and calcium phosphate series, substantially with non-sodium oxide.

Description will be made below as to the reason why the amount of each component of the biocompatible crystallized glass of the present invention is limited to the above described range.

$SiO_2$ is one of components of the tetrasilicic fluorine mica series crystalline ($KMg_{2.5}Si_4O_{10}F_2$) and is used for increasing strength of a glass matrix phase. When $SiO_2$ amount is less than 40.0%, the glass tends to be softened and deformed at a crystallizing heat-treatment. If $SiO_2$ amount is more than 70.0%, it is hard to melt the glass so that a uniform glass could not be obtained.

$MgO$ is one of components of tetrasilicic fluorine mica series crystalline. When $MgO$ amount is less than 5.0%, amount of tetrasilicic fluorine mica series crystalline remarkably decreases. A resultant glass exhibits substantial degradation of strength due to a flaw. If $MgO$ amount is more than 34.0%, heterogenetic crystalline deposites or precipitates, similar to enstatite ($MgOSiO_3$) at the crystallizing heat-treatment. The resultant glass is cloudy and is not beautiful in its appearance.

F is another one of the components of tetrasilicic fluorine mica series crystalline. When F amount is less than 1.8%, the amount of tetrasilicic fluorine mica series crystalline decreases substantially. A resultant glass has much degradation of strength due to a flaw. If F amount is more than 11.0%, the glass tends to be softened and deformed at the crystallizing heat-treatment.

$Al_2O_3$ is used for stabilizing calcium phosphate series crystalline and increasing chemical resistance. When $Al_2O_3$ is more than 2.0%, heterogenetic crystalline deposits, like $Mg_2Al_4Si_5O_{18}$, at the crystallizing heat-treatment. A resultant glass is also cloudy and is not beautiful in its appearance due to precipitation of the heterogenetic crystalline, with excessive hardness.

$K_2O$ is another of components of tetrasilicic fluorine mica series crystalline. When $K_2O$ amount is less than 4.0%, a resultant glass is also cloudy and does not have a beautiful appearance by precipitation of the heterogenetic crystalline, similar to enstatite ($MgOSiO_3$). If $K_2O$ amount is more than 20.0%, large crystalline of mica series deposits at the crystallizing heat treatment. Moreover, the resultant glass does not have uniformity.

$ZrO_2$ is used for controlling the size of the tetrasilicic fluorine mica series crystalline. When $ZrO_2$ is more than 7.0%, heterogenetic crystalline deposits similar to enstatite ($MgOSiO_3$). The resultant glass is cloudy due to precipitation of the heterogenetic crystalline.

$CaO$ and $P_2O_5$ are components of calcium phosphate series crystalline and used for increasing biological affinity. Amount of each of them must be 0.01–20.0%. When the amount of each of $CaO$ and $P_2O_5$ is less than 0.01%, the glass is insufficient in the biological affinity because calcium phosphate series crystalline hardly deposits, similar to apatite crystalline ($Ca_{10}(PO_4)_6O$) or tricalcium phosphate ($3CaOP_2O_5$) and so on. If each of $CaO$ and $P_2O_5$ amounts is more than 20.0%, the resultant glass is devitrifiable and it is hard to obtain a uniform glass. Moreover, large grains of apatite crystalline deposit tend to degrade the appearance of the glass.

On the other hand, the biocompatible glass of this invention is characterized by a color tone of semi-opacity as an opal glass and similar to the natural tooth. Even if the color tone of the glass is little bit different from various human natural teeth, it is possible to make the color tone of the glass correspond to any of the natural teeth.

One method of coloring is use of a coloring agent such as $CeO_2$, $MnO_2$, transition metal oxide, noble metal oxide, noble metal halogenide, noble metallic salt and/or others. The coloring agent amount is preferably 0.01–8% against 100% glass by weight. When the coloring agent amount is less than 0.01%, the agent could not be effective to change the color tone of the glass. If the coloring agent amount is more than 8%, the color tone of the glass change to dark color.

Another method is to coat the glass with a desired glaze.

This biocompatible crystallized glass of this invention can be added by any component as long as it is adaptive to the tetrasilicic fluorine mica series or the calcium phosphate series. The component is, for example, oxide of metals in the first (excluding sodium oxide) or the second group of the periodic table and transitional metal oxide.

Still more, according to the present invention, the glass is substantially free of $Na_2O$. Because a uniform glass could not be obtained and the glass appearance is not beautiful by large grain growth of tetrasilicic fluorine mica series crystalline.

EXAMPLES

Table 1 demonstrates ingredients of various biocompatible glass according to the present invention and their properties, that is, biological affinity, bending strength, and appearance.

TABLE 1

(weight %)

| Ingredients | Sample No. | | | | | | | |
|---|---|---|---|---|---|---|---|---|
| | 1 | 2 | 3 | 4 | 5 | 6 | 7 | 8 |
| $SiO_2$ | 57.2 | 61.7 | 57.1 | 47.1 | 52.0 | 53.9 | 59.7 | 33.5 |
| MgO | 17.3 | 15.9 | 11.7 | 21.5 | 15.3 | 16.6 | 17.8 | 3.8 |
| F | 5.5 | 5.6 | 5.9 | 5.0 | 6.0 | 5.2 | 5.0 | — |
| $Al_2O_3$ | — | 1.8 | — | — | 1.8 | — | — | 4.7 |
| $K_2O$ | 12.5 | 11.5 | 13.0 | 12.8 | 17.0 | 12.2 | 12.9 | — |
| $ZrO_2$ | 4.5 | — | 4.8 | 4.2 | — | 4.5 | 4.6 | — |
| CaO | 1.6 | 1.9 | 3.1 | 6.0 | 2.8 | 2.1 | — | 41.8 |
| $P_2O_5$ | 1.4 | 1.6 | 2.6 | 3.4 | 5.1 | 3.6 | — | 16.2 |
| | | | | $CeO_2$ 1.8 | | $Fe_2O_3$ 1.9 | | |
| Biological Affinity | Excellent | Excellent | Excellent | Excellent | Excellent | Excellent | Good | Excellent |
| Bending Strength ($kg/cm^2$) | 1650 | 1400 | 1800 | 1450 | 1500 | 1500 | 1400 | 700 |
| Appearance | Good | Good | Excellent | Good | Good | Excellent | Good | Good |

Each sample was produced as follows. Each raw glass material or glass batch was prepared in accordance with ingredients of Table 1. The raw glass material was inserted in a platinum crucible and was melted in an electric furnace at temperature of 1300°–1550° C. (preferably, about 1450° C.) for 2–6 hours (preferably, about 4 hours). Then, the molten glass was formed into a solid piece of desired shape by casting. The solid piece was heated in an electric furnace at temperature between about 600°–1150° C. (preferably, about 1050°–1075° C.) for about 1–10 hours (preferably, about 4 hours), and a biocompatible crystallized glass sample was obtained.

Referring to Table 1, samples Nos. 1–6 represent glasses according to the present invention, and samples Nos. 7 and 8 represent glasses according to the prior art.

Test 1

Each of samples Nos. 1–6 was confirmed by the powder X-ray reflection method to have a number of tetrasilicic fluorine mica series crystalline and apatite crystalline. Those crystallines were confirmed by the scanning electron microscope to interlace and to be dispersed in the glass phase.

On the other hand, sample No. 7 only had a number of tetrasilicic fluorine mica series crystalline, and sample No. 8 had a number of apatite crystalline.

Test 2

Each of samples Nos. 1–8 was formed to be a plate body having a size of 8×1 mm and a plate body having a size of 3×4×36 mm.

Each plate body was measured for a biological affinity by culturing a human integument fibroblast on both surfaces each of which was polished surface and was a coarse surface of its plate bodies for 48 hours at 37° C., respectively.

Further, each sample was measured for a bending strength by using a 3×4×36 mm plate body by the three-point loading test with 30 mm span at 0.5 mm/min cross-head speed after causing abrasion on the plate body by an abrasive paper.

The result is also shown in Table 1. As is seen from Table 1, the samples Nos. 1–6 of the present invention has an excellent biological affinity and a high bending strength in comparison with samples Nos. 7 and 8 of the prior art.

Test 3

Each molten glass mentioned above was cast by lost wax process as follows.

A paraffin wax was inserted in an original mold and then, hardened or cured to form a wax model. Then, the wax model was deposited a sprue line made of paraffin and was sunk in an investment slurry which was made of ethyl silicate series. After the investment slury was hardened or cured, the investment slury, the sprue line, and the wax model were gradually heated to an elevated temperature of 120°–150° C. and were incinerated. Then, the investment slurry, the sprue line, and the wax model were gradually heated to an elevated temperature of 700°–800° C. and was kept for a desired time, and a casting mold was obtained.

On the other hand, the molten glass was divided to be a number of small blocks and was re-melted at 1300°–1500° C.

The molten glass was injected into the casting mold and was formed as a glass body by a centrifugal casting machine.

After being put out from the casting model, the glass body was heated at about 1000°–1100° C. for about 4 hours.

When the glass body of each of samples Nos. 1–8 was visual-observed, the fact was confirmed that any sample glass body has a good semiopacity as shown in Table 1, especially, samples Nos. 3 and 6 has an excellent color tone similar to a natural tooth and an excellent beautiful appearance because of adding the coloring agent.

What is claimed is:

1. A high-mechanical strength biocompatible crystallized glass consisting essentially of both crystallines of tetrasilicic fluorine mica series and calcium phosphate series, said crystalline glass being free of sodium oxide.

2. A biocompatible crystallized glass as claimed in claim 1, having composition which consists essentially by weight of:
40.0–70.0% $SiO_2$,
5.0–34.0% $MgO$,
1.8–11.0% $F$,
0–2.0% $Al_2O_3$,
4.0–20.0% $K_2O$,
0–7.0% $ZrO_2$,
0.01–20.0% $CaO$, and
0.01–20.0% $P_2O_5$.

3. A biocompatible crystallized glass as claimed in claim 1, having composition which consists essentially by weight of:
42.0–65.0% $SiO_2$,
7.0–25.0% $MgO$,
2.5–8.0% $F$,
0–1.9% $Al_2O_3$,
8.0–18.0% $K_2O$,
0–6.0% $ZrO_2$,
0.5–10.0% $CaO$, and
0.5–10.0% $P_2O_5$.

* * * * *